United States Patent
Klicker

[11] Patent Number: 5,917,933
[45] Date of Patent: Jun. 29, 1999

[54] METHOD AND DEVICE FOR CARRYING OUT THE QUALITY CONTROL OF AN OBJECT

[75] Inventor: Jürgen Klicker, Hoisdorf, Germany

[73] Assignee: Basler GmbH, Germany

[21] Appl. No.: 08/531,578

[22] Filed: Sep. 21, 1995

[30] Foreign Application Priority Data

Sep. 27, 1994 [DE] Germany ................... 4434475

[51] Int. Cl.⁶ ................................... G06K 9/00
[52] U.S. Cl. ............... 382/149; 382/227; 348/125
[58] Field of Search ................... 382/141–145, 382/149, 226, 227; 348/86, 92, 125, 127, 128; 356/237, 239, 240; 364/468; 250/222.2

[56] References Cited

U.S. PATENT DOCUMENTS

| | | | |
|---|---|---|---|
| 4,030,835 | 6/1977 | Firester et al. | 356/111 |
| 4,197,011 | 4/1980 | Hudson | 356/354 |
| 4,505,585 | 3/1985 | Yoshikawa et al. | 356/237 |
| 4,674,875 | 6/1987 | Koizumi | 356/237 |
| 4,741,044 | 4/1988 | Polomsky et al. | 382/149 |
| 4,848,864 | 7/1989 | Ostertag et al. | 250/235 |
| 4,954,723 | 9/1990 | Takahashi et al. | 250/572 |
| 4,957,367 | 9/1990 | Dulman | 356/359 |
| 4,974,261 | 11/1990 | Nakahara et al. | 382/22 |
| 5,016,099 | 5/1991 | Bongardt et al. | 358/106 |
| 5,031,112 | 7/1991 | Sakai et al. | 364/507 |
| 5,194,746 | 3/1993 | Coen et al. | 250/563 |
| 5,268,735 | 12/1993 | Hayashi | 356/237 |
| 5,434,838 | 7/1995 | Haneda | 369/58 |

FOREIGN PATENT DOCUMENTS

| | | |
|---|---|---|
| 0 087 795 | 9/1983 | European Pat. Off. . |
| 3800053 A1 | 7/1989 | Germany . |
| 3816392 | 11/1989 | Germany . |
| 3919330 A1 | 12/1989 | Germany . |
| 3842636 | 6/1990 | Germany . |
| 3937950 A1 | 7/1990 | Germany . |
| 4123916 | 1/1992 | Germany . |

OTHER PUBLICATIONS

Abstract of DE 4123916 in English Language Jan. 23, 1992.

Primary Examiner—Christopher S. Kelley
Attorney, Agent, or Firm—Howson & Howson

[57] ABSTRACT

The invention pertains to a method and a device (60) for carrying out the quality control of an object (10). According to this method, at least a partial region of the object is scanned by means of at least one optical scanning system (40), and the gray scale values of the scanned points are recorded and stored. The gray scale values of at least part of the points are evaluated by an evaluation unit (64). In order to attain a faster display of the object (10), the invention proposes that at least part of the recorded gray scale values are stored in a storage unit (62), that at least one respective point is classified as being possibly defective or flawless based on its gray scale value in a filter unit (63) that is arranged in front of the evaluation unit (64), and that at least the points that were classified as being possibly defective are evaluated by the evaluation unit (64) based on the measured data stored in the storage unit (62).

17 Claims, 4 Drawing Sheets

METHOD AND DEVICE FOR CARRYING OUT THE QUALITY CONTROL OF AN OBJECT

BRIEF SUMMARY OF THE INVENTION

The invention pertains to a method for carrying out the quality control of an object in which at least a partial region of the object is scanned by means of at least one optical scanning system and the gray scale values of the scanned points are recorded, with the gray scale values of at least part of the points being evaluated by an evaluation unit. The invention also pertains to a device for carrying out the quality control of an object. The invention in particular pertains to the optical quality control of a compact disc (CD); i.e., the following description primarily refers to a CD, but the invention is not limited to this particular type of application.

Lately, CDs have become more and more popular because these sound carriers yield a very high sound quality in domestic use. However, they are also used as pure data carriers for data processing systems because of their high data density. Last but not least, their relative insensitivity to external influences represents one additional reason for the continued popularity of CDs. Consequently, a CD unquestionably represents a mass product which, however, needs to fulfill the strictest quality requirements.

There exist numerous methods for measuring the different defects that can occur during the manufacture of a CD. Due to the physical design of a CD, namely a transparent layer and a reflective layer arranged behind said transparent layer, optical measuring methods and measuring devices which are also the object of this invention are particularly suitable for this purpose.

The initial description pertains to the design and the manufacture of a CD as well as the possible defects that can occur during the manufacturing process. A CD consists of a circular disc, in the center of which an aperture is arranged for centering [the CD] in a CD player. Viewed from the bottom, i.e., the reading side of the CD player, toward the top, the cross section of this disc consists of a transparent plastic layer that is generally manufactured of polycarbonate and already contains all information in the form of pits. A metallic layer that usually consists of aluminum and serves for rendering the surface of the polycarbonate layer reflective is arranged on top of the aforementioned transparent plastic layer such that the information can be read by the optical scanning system of the CD player. This very thin metallic layer is protected by a coat of lacquer that is also very thin and usually hardened by means of UV light. Lettering or the like can be arranged on this coat of lacquer in order to label the CD.

Viewed in the radial direction, a CD has several coaxial annular regions that originate from the central aperture and extend outward. The region that serves for clamping the CD in the CD player is situated directly on the central aperture. A region that carries the so-called identification code that serves for conclusively identifying the CD is situated adjacent to the aforementioned region. The region that serves for storing the data is situated adjacent to the region carrying the identification code. If the CD is prerecorded to its maximum storage capacity, this region ends directly at the outer border region. Otherwise, the so-called lead-out or an image band is arranged between the outer edge region of the CD and the data region.

When manufacturing a [CD], a blank is initially manufactured from polycarbonate by means of die casting, with all information already being impressed by means of the die plate. Subsequently, one surface of the blank is provided with the metallic reflective layer by means of sputtering and sealed with the coat of lacquer. The CD is centrifuged during these processes in order to realize the uniform distribution of the aluminum layer and the coat of lacquer and to obtain the thinnest possible layer. Subsequently, the label is printed onto the CD.

It is obvious that the reflective layer and the transparent polycarbonate body need to be flawless with respect to their optical properties due to the high data density of the CD that is read in an optical fashion. The slightest defects, in particular within the data region, can already cause significant interferences during the reading process; i.e., unacceptable aberrations can result, particularly if [the CD] is used for data processing. Consequently, it is practical as well as necessary to incorporate a quality control that makes it possible to detect and classify the possible defects of a CD into the production process such that a subsequent elimination of the defective CDs or a rectification of the production process can be carried out.

The following defects can occur: holes in the reflective layer, so-called pinholes, are created by a dust particle or the like which is present on the surface before the sputtering process and thrown outward while entraining a piece of the metallic surface during the centrifuging of the CD. Aluminum scratches occur if the dust particle remains on the surface while it is thrown outward and consequently causes additional damage to the metallic layer. Underneath the metallic layer, organic residues, e.g., oil stains, can lead to scanning errors. So-called pimple defects are created if the polycarbonate blank is deformed on the side that must be coated. Inclusions of foreign matter in the polycarbonate layer are called black spots. Bubbles, air inclusions or the like can also be present in the polycarbonate layer. In addition, the underside of the CD can contain lacquer splashes or scratches that are caused by mechanical influences and lead to reading errors or diminish the sound quality.

Depending on their size, these defects always cause optical aberrations, which can usually be detected with customary inspection apparatuses. However, a classification of the defects also requires that the depth of the respective defects be determined. Consequently, it is necessary to utilize measuring methods and measuring devices that are able to measure the defects in a three-dimensional fashion. Depending on the data density, it is, at least within the data region, also required to carry out the tests with a deep inspection level; i.e., a local resolution within the range between 30 $\mu$m and 50 $\mu$m needs to be attained. Outside of the data region, only defects that influence the optical appearance of the CD are important. In this case, a lower inspection level, e.g., with a local resolution of approximately 200 $\mu$m, which corresponds with that of the human eye, would suffice.

In order to detect these defects, there exist measuring methods and measuring devices in which the CD is scanned by means of an optical scanning system. In this case, a linear light beam is projected onto the underside at an acute angle, reflected and recorded by a so-called line camera. The line camera comprises a linear receiver that is divided into several adjacent picture elements. The defect appears in the camera or on the monitor of the evaluation unit in the form of a dark spot or a spot that has a different gray scale value. The CD carries out one revolution during the test and is usually illuminated with approximately 6,000 lines during this revolution. Due to the distinct geometry and the predetermined revolution of the CD, one can simultaneously draw conclusions as to the depth of a defect, since the same defect appears twice at the same location during the revolution [of the CD], namely because said defect lies in the incident light beam as well as in the reflected light beam.

The measured values of a point on the CD which are recorded by the camera are evaluated in the form of a video signal in a data processing system which detects possible defects and classifies their depth with the aid of the gray scale values and the location of said point. It is quite obvious that smaller defects also need to be detected due to the continuously increasing data density of a CD, i.e., it is required to scan a CD with a continuously increasing number of test points. However, this results in a continuously increasing quantity of data that needs to be processed by the data processing system.

It is obvious that the processing of such a large quantity of data requires a significant computing time, even if high-speed computers are utilized. This means that a test with the required point density can frequently not be easily integrated into the production process. Consequently, lower local resolutions are still utilized for the quality control, in particular for time reasons. However, this is associated with the disadvantage that smaller defects within the data region which can lead to reading errors are not detected or only classified insufficiently.

The invention is based on the objective of developing a method and a device which make it possible to test an object with the desired local resolution within a shorter time.

According to the invention, this objective is attained due to the fact that at least part of the recorded gray scale values are stored in a storage unit, that at least one respective point is, with the aid of its gray scale value, classified as being possibly defective or flawless in a filter unit that is arranged in front of the evaluation unit, and that at least the points that are classified as being possibly defective are evaluated by the evaluation unit based on the measured values stored in the storage unit. This provides the advantage that the stored gray scale values are initially presorted such that a smaller quantity of data needs to be processed during the evaluation. Consequently, a reliable reduction of the picture points to be processed is carried out; i.e., the computing time of the evaluation unit can be significantly reduced.

According to this method, only the points that were classified as being probably defective are transmitted from the filter unit to the evaluation unit. For this purpose, one can utilize an uncomplicated electronic circuit that carries out this simple allocation within a short time, namely also for large quantities of data. According to one embodiment of the invention, it is proposed that the respective gray scale value of at least one point is compared with at least one predetermined reference value and/or range of reference values in the filter unit. In addition, it is also possible to link the respective gray scale values of at least two points with one another in the filter unit and compare the linkage result with a predetermined quantity of reference linkage results, with at least one of said points being classified as being possibly defective in case of a deviation. In this case, it is practical to link the respective gray scale values of two adjacent points with one another.

It is, in principle, possible to link the gray scale values of the points with one another in an arbitrary fashion. However, it is practical to link the points in such a way that a classification which is essentially independent of the exposure intensity is possible. It is, for example, possible to deduct the gray scale values from one another, wherein the difference cannot exceed or fall short of a predetermined range. However, it can also be practical if the quotient of the gray scale values is formed, wherein the linkage result needs to lie within at least one predetermined range. The filter unit allows such a linking between two or a few values and measured or predetermined values within a short time without requiring a complicated evaluation.

Naturally, it is also possible to not only compare the gray scale values of a certain number of points with one another, but additionally compare said gray scale values with a predetermined threshold value or range of values. Consequently, defects with floating transitions can also be marked for subsequent evaluation. In such defects with floating transitions, the difference of the gray scale value as compared to the adjacent point is relatively low because the threshold value of the gray scale value of a point is, for example, exceeded or fallen short of during the course of the classification. These operations can also be carried out in the filter unit within a short time, namely also for large quantities of data.

Consequently, the filter unit determines the points or the range of points the gray scale values of which do not correspond with the predetermined values or range of values for a flawless point or range. This measure makes it possible to define the ranges within which a possible defect may lie before the generally time-consuming evaluation process. The evaluation as to the fact of whether a defect is present or not is, for example, limited to a range that was previously marked by the filter unit. In this case, it is practical if the evaluation unit also evaluates the gray scale values of the points within the region that surrounds the point that was detected by the filter unit so as to be able to delimit distinctly and classify a possible defect.

The data and gray scale values of the other measuring points that were not marked by the filter unit and are not situated in the surrounding or limited point range are not processed by the evaluation unit and appear on the monitor in the form of flawless zones.

Consequently, the quantity of data that needs to be processed by the evaluation unit can be significantly reduced, e.g., to approximately 10% of the total picture data. This also makes it possible to reduce significantly the time required for generating the image of the tested CD.

According to one embodiment of the invention, it is proposed that the evaluation of the gray scale values be carried out with different inspection levels within the different regions of the object. Because only the data region of a CD needs to be tested with a high inspection level, the quantity of data can be additionally reduced by means of a corresponding reduction of the inspection level and, consequently, the number of measuring points within the other regions.

In this case, it is practical if the different regions of the object are identified by the evaluation unit based on the different gray scale values of these regions. This is possible because the different regions, e.g., of a CD, have different gray scale values such that at least the borders of said regions can be detected by means of the filter unit. The determined border points of the respective regions then result in an essentially concentric circle around the central axis of the CD such that the evaluation unit can automatically adjust the required and possibly predetermined inspection levels in accordance with these border points.

According to one practical embodiment of the invention, it is proposed that the optical scanning be carried out by means of a linear light beam, and that the gray scale values be recorded by at least one line camera. In this case, it is practical if the photosensitive receiver comprises at least 1,024 picture elements. However, it is particularly advantageous if the photosensitive receiver of the camera used comprises at least 2,048 picture elements. This provides the advantage that the local resolution in the direction of the light beam, i.e., in the radial direction of a CD, can be significantly increased by utilizing the presorting of the data by the filter unit for faster data processing. Consequently, an extension of the predetermined test time during the production process is not required.

It is obvious that, when testing a CD with the generally utilized radial beams, the distance between the beams in the circumferential direction continues to increase as the distance from the central axis increases, i.e., significant defects possibly cannot be detected, in particular within the outer edge region. Because the invention makes it possible to process large quantities of data within a short time, one advantageous embodiment proposes that the entire surface of the CD is scanned with at least 10,000 lines. This measure makes it possible to also detect smaller defects within the edge region. Depending on the design of the camera used, the number of illuminated lines can also amount to approximately 12,000.

It is, in principle, possible to utilize arbitrary cameras and illumination types in connection with one another. In any case, the classification of the gray scale values before their evaluation not only makes it possible to use cameras that have a high local resolution, but also cameras that simultaneously operate in a rapid fashion. This makes it possible to evaluate a larger quantity of picture points and process the data more rapidly. It is, in particular, also possible to attain a significantly higher local resolution with longer test durations. The quantity of data that can be processed according to the invention consequently only depends on the maximum computing speed of the processor used.

Because the invention makes it possible to process large quantities of data within a very short time, it is additionally proposed that the complete revolution for the complete illumination of the CD take place within 0.25 to 2.5 sec. This short illumination time and the short subsequent processing time of the measured values allows an uncomplicated integration of the quality control into the production process.

The device for testing an object, in particular a CD, comprises at least one scanning element for carrying out an optical scanning process and at least one recording element for recording the gray scale values of the scanned points of at least a partial region of the object, with the recording element being connected with an evaluation unit for the gray scale values of the points. According to the invention, it is proposed that at least one storage element for storing at least part of the recorded gray scale values be provided, and that a filter element for classifying the points based on their gray scale values before they are transmitted to the evaluation unit be arranged between the scanning element and the evaluation unit. The filter unit is able to reduce significantly the quantity of data that needs to be processed by the evaluation unit.

According to one advantageous embodiment, it is proposed that the filter element comprise an electronic circuit that is switched in such a way that the respective gray scale values of two preferably adjacent points are linked with one another. A fixed electronic circuit makes it possible to carry out the required classification of the gray scale values, namely a classification as to the fact if the gray scale values of the two points in question deviate from one another, with a very high speed. The presorting of the measured gray scale values consequently requires hardly any time, and the time required for the evaluation of the gray scale values in the evaluation unit is also reduced due to the reduced quantity of data. Consequently, the test device easily can be integrated into the production process.

It can also be practical if the filter element comprises an electronic circuit that is switched in such a way that the respective gray scale value of at least one point is compared with at least one predetermined reference value and/or range of reference values. This measure makes it possible to reliably detect defects with undefined borders.

In particular when testing rotationally symmetrical or circular objects, e.g., CDs, it is practical if the scanning element comprises at least one light source for generating a linear light beam. This measure makes it possible for the light beams to extend radially from the central axis such that an illumination of the entire surface can be realized simply by revolving the object once.

In order to attain a high local resolution, it is proposed that the recording element comprise a photosensitive receiver with at least 1,024 picture elements in one line. However, it is particularly practical and, due to the reduction of the quantity of data to be processed by the filter unit, also possible that the recording element comprise a photosensitive receiver with at least 2,048 picture elements in one line. This measure makes it possible to increase significantly the point grid such that smaller defects can also be detected.

BRIEF DESCRIPTION OF THE DRAWINGS

The invention is described in detail below with reference to the schematic figures. The figures show.

DETAILED DESCRIPTION

Figure 1:
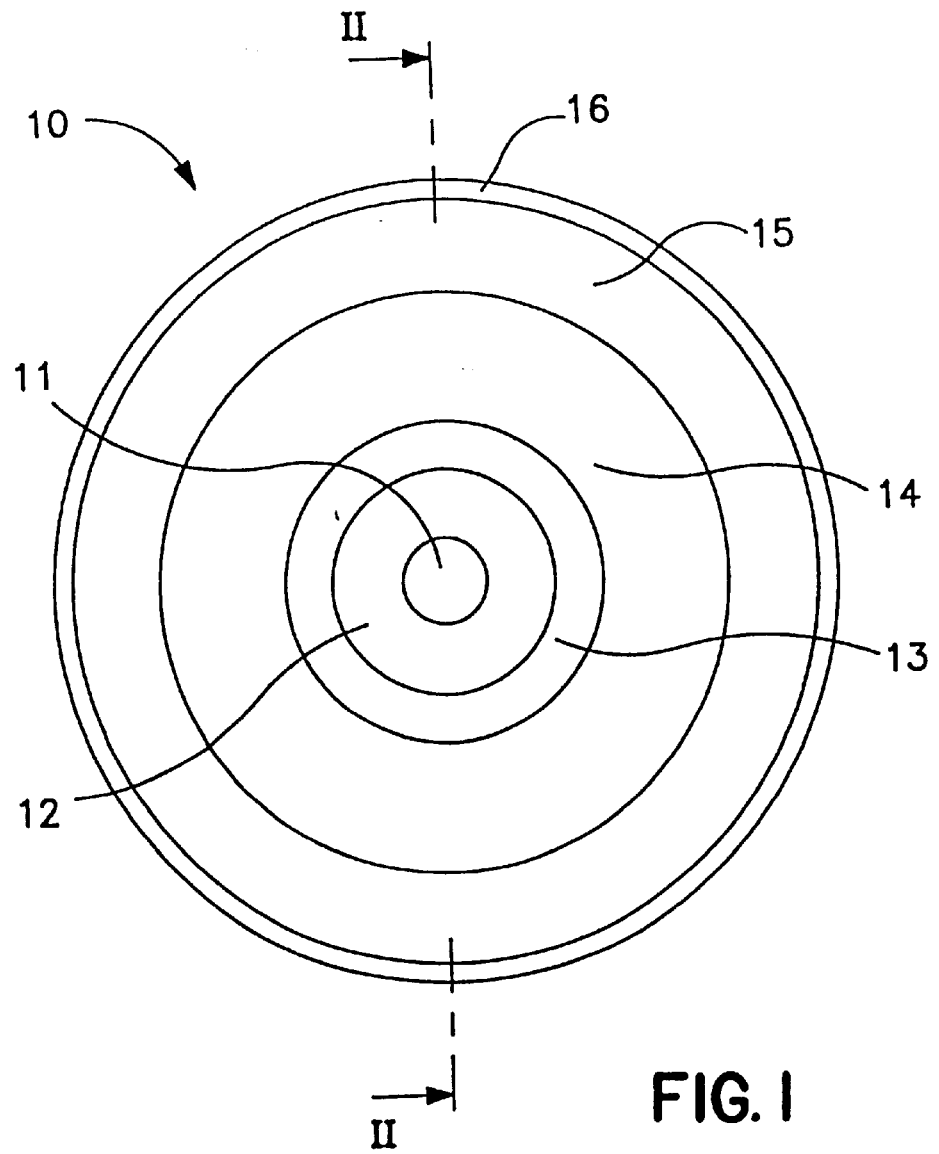
FIG. 1, a top view of a compact disc.
Figure 2:
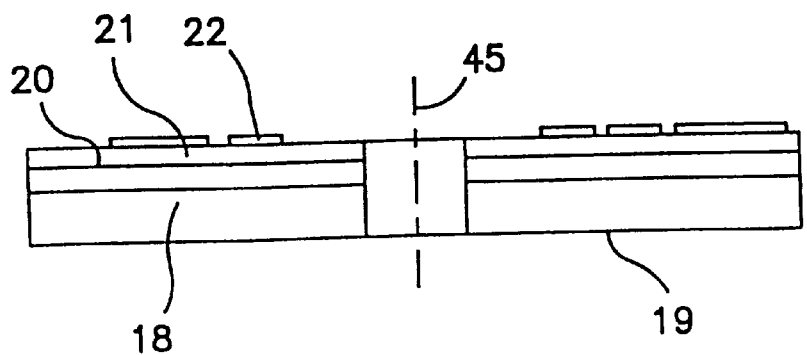
FIG. 2, a cross section through a compact disc along the line II—II in FIG. 1.

FIGS. 1 and 2 schematically illustrate the design of a CD 10. CD 10 comprises various regions in the radial direction as shown in FIG. 1. Viewed from the inside toward the outside, one can observe the central aperture 11 for centering the CD in the CD player and the inner edge region 12 for clamping the CD in the CD player. A region 13 that carries the identification code and is surrounded by the data region 14 is situated adjacent to the aforementioned inner edge region. Depending on the degree of recorded information, a lead-out 15 or the outer edge region 16 of the CD are situated adjacent to the data region 14.

Viewed in the axial direction from the bottom toward the top (FIG. 2), the CD 10 comprises a transparent polycarbonate layer 18 that is provided with a metallic layer 20 on the side opposite to the underside 19. Consequently, a reflective surface is created such that the data that is stored within the polycarbonate layer in the form of (not shown) pits can be scanned by optical means in the CD player from the underside 19. The metallic layer 20 is sealed with a coat of lacquer 21 on the side that is opposite to the polycarbonate layer 18, with a color layer 22 in the form of a label being printed on said coat of lacquer.

Figure 3:
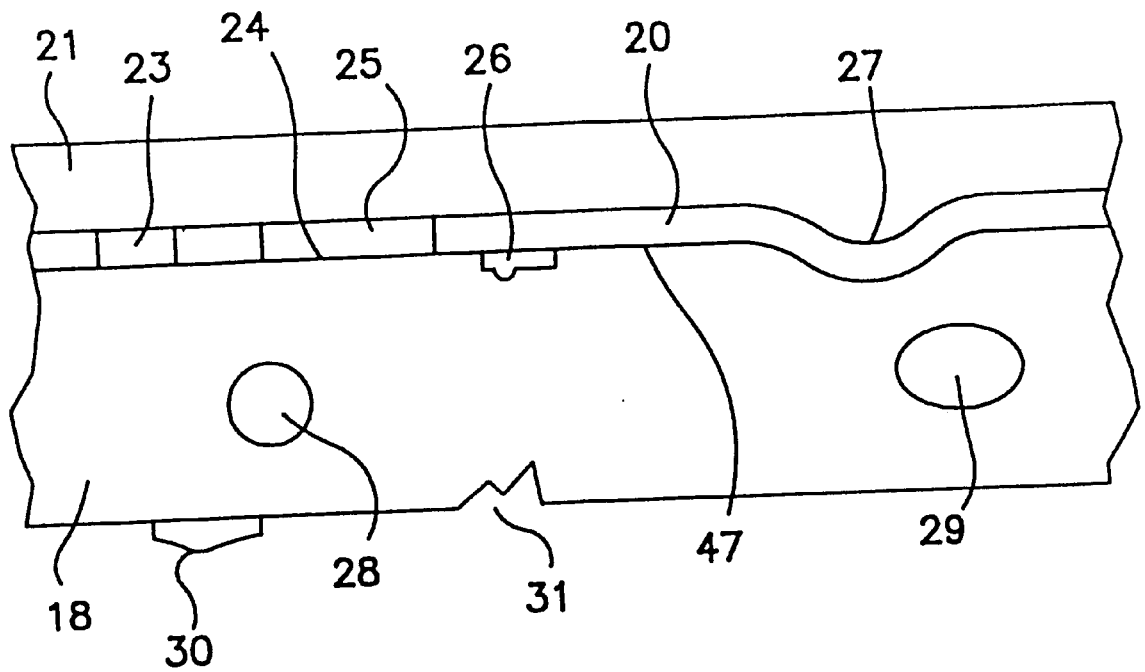
FIG. 3, a schematic representation of the possible defects in a compact disc.

FIG. 3 shows the possible defects that might occur during the manufacture of a CD and can be displayed by means of customary measuring methods. The reference numeral 23 identifies so-called pinholes, which are caused by dust particles that are situated on the surface 24 of the polycarbonate blank, separate from the surface while the CD is centrifuged during the sputtering process and entrain a piece of the metallic layer 20 during this process. The so-called aluminum scratches 25 are created in the same fashion, but the dust particle initially continues to travel outward on the surface 24. The oil stains 26 represent organic residues on the surface 24 of the polycarbonate layer 18 of the CD 10. A so-called pimple defect 27 is caused by a deformation of the polycarbonate blank 18. Black spots 28 due to inclusions of foreign matter or bubbles 29 due to gas inclusions can also be present within the polycarbonate layer 18. Lacquer splashes 30 or scratches 31 caused by external mechanical influences can occur on the underside 19 of the polycarbonate layer. These defects diminish the intensity of the test light beam such that black regions or regions with different gray scale values become visible at the respective locations of the graphic illustration.

Figure 5:
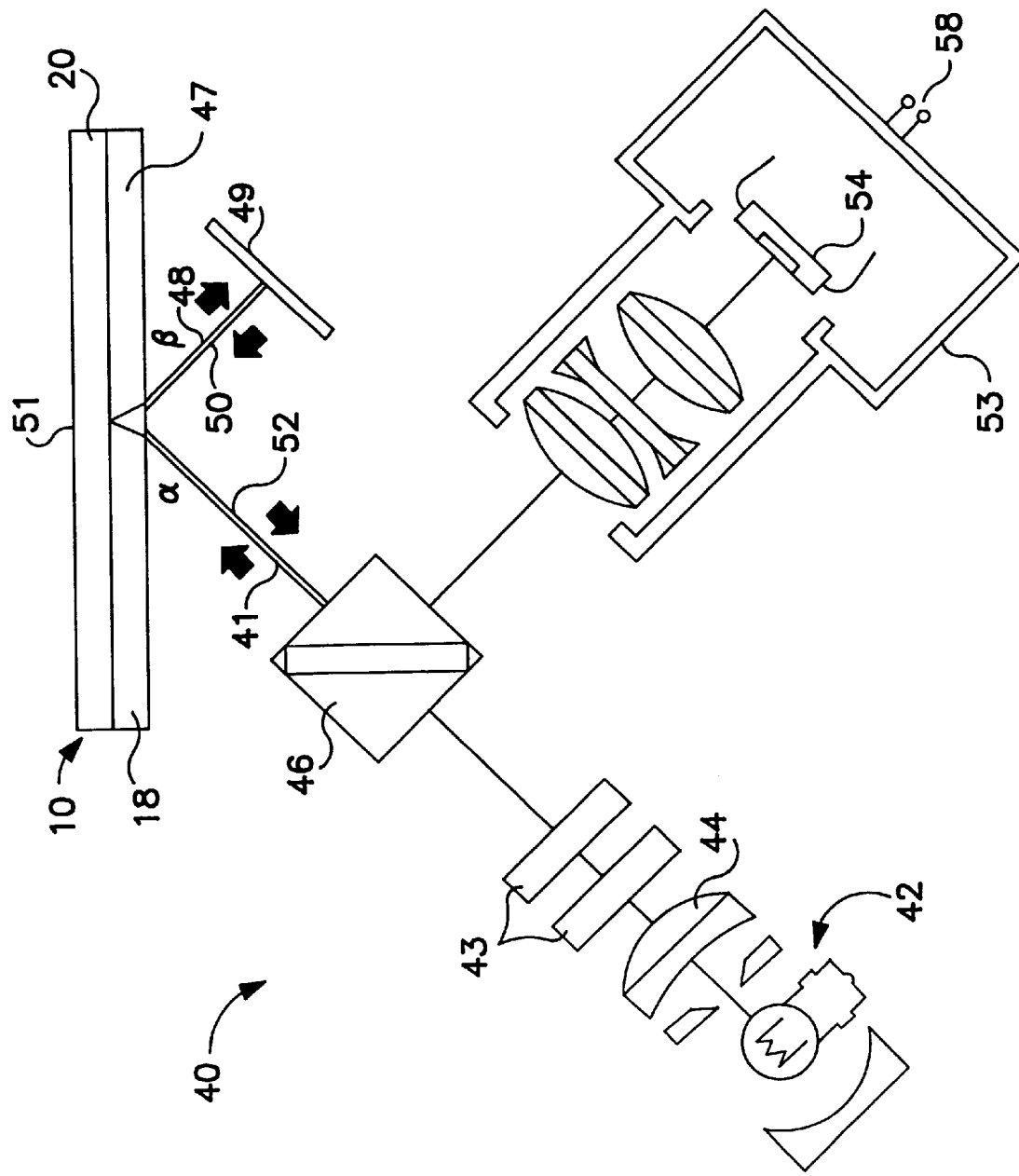
FIG. 5, the scanning system of a device according to the invention.

FIG. 5 schematically shows a scanning device 40 for carrying out the quality control of CDs 10. This illustration is limited to the progression of the light beam 41, because a person skilled in the art is familiar with the required design, the angles to be observed, etc.

Figure 4:
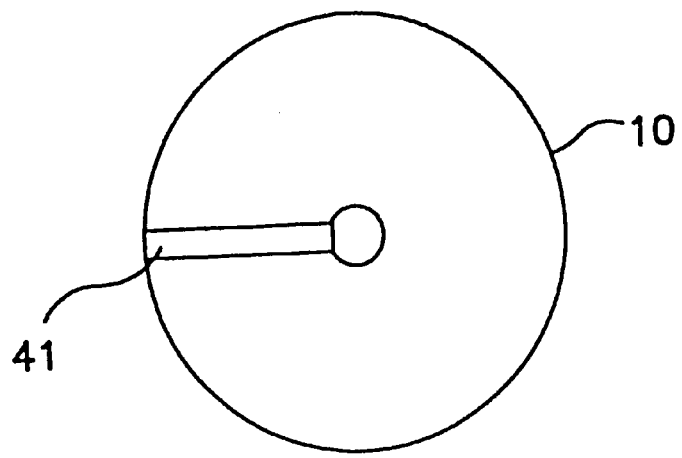
FIG. 4, a top view of a CD that is illuminated by a light beam.

The scanning device 40 comprises a light source 42 that, for example, can be realized in the form of a customary halogen lamp. A light beam 41 that has a linear shape referred to the surface of the CD 10 and is projected onto the underside 19 of the CD 10, i.e., the reading side, in the form of a beam that originates radially from the central axis 45, can be generated with an arrangement of various generally known diaphragms and lenses 43, 44. During the test, the CD revolves around this central axis 45. The linear illumination of the CD 10 is illustrated in FIG. 4. Naturally, it is also possible that this light beam extend over the entire diameter of the CD 10. In this case, only one-half revolution of the CD 10 would be required for carrying out a comprehensive test.

A beam splitter 46 is arranged between the light source 42 and the CD 10 in the direction of the light beam 41. Part of the light beam 41 initially passes through said beam splitter without being deflected, is projected onto the underside 19 of the transparent layer 18 of the CD 10, i.e., the polycarbonate layer, and refracted at this location in accordance with the optical properties of this layer. The angle of incidence α is chosen such that no total reflection occurs on the underside 19 of the polycarbonate layer 18, e.g., between 30° and 60°. The light beam 41 is reflected on the reflective surface 47 formed by the metallic layer 20 and, after being refracted correspondingly, emerges from the polycarbonate layer 18 at the same angle of reflection β.

A mirror element 49 that is aligned in such a way that it reflects the incident light beam 48 in exactly the opposite direction, i.e., [such that] a light beam 50 that extends opposite to the reflected light beam 48 is created, is arranged subsequently in the path of the reflected light beam 48. In order to prevent any misunderstanding, it should be emphasized that the different light beams are only illustrated adjacent to one another for reasons of elucidation. If the optical system is adjusted correctly, the light beams extend on top of one another.

This light beam 50 is again refracted in accordance with the optical properties of the transparent layer 18 and reflected on the reflective surface at the same point 51 at which the incident light beam has already been reflected. Because of this arrangement, the light beam passes over the CD 10 twice, namely once in the form of the original light beam 41 and the second time in the form of the light beam 50 that was reflected by the mirror element 49, in one measuring position, i.e., the CD 10 does not carry out an additional revolution.

It is quite obvious that this measure makes it possible to display low-contrast defects, because the same light beam is diminished twice by the same defect such that the contrast is increased as compared to the adjacently extending undisturbed beams. It is, in particular, also possible to detect the various regions 13, 14, 15, 16 of the CD 10, which frequently only differ slightly with respect to their gray scale values in a simpler fashion.

The emerging light beam 52 is projected onto the beam splitter 46 in which said light beam is split in accordance with the design and alignment of the beam splitter 46. In the embodiment shown in the figure, part of the reflected light beam 52 is deflected by approximately 90°. A photosensitive receiver that is realized in the form of a line camera 53 in this embodiment is arranged behind the beam splitter 46 viewed in the direction of deflection. The line camera 53 comprises a customary linear receiver 54 that is at least partially exposed by the linear light beam, which is reflected several times. Possible defects of the CD 10 are displayed in the form of dark spots or spots that were not exposed as intensely.

The video output 58 of the line camera 53 is connected with a data processing system 61. This data processing system 61 also determines the depth of the determined defect, namely by detecting that the same darkening appears at the same location while the CD 10 is situated in different angular positions. In addition, the data is evaluated as to whether the various radial regions of a CD 10 are detected so as to make it possible to operate with an increased inspection level within the data region 14. In addition, it is possible that the light beam also illuminates the region carrying the identification code which can be subsequently evaluated in the data processing system.

Figure 6:
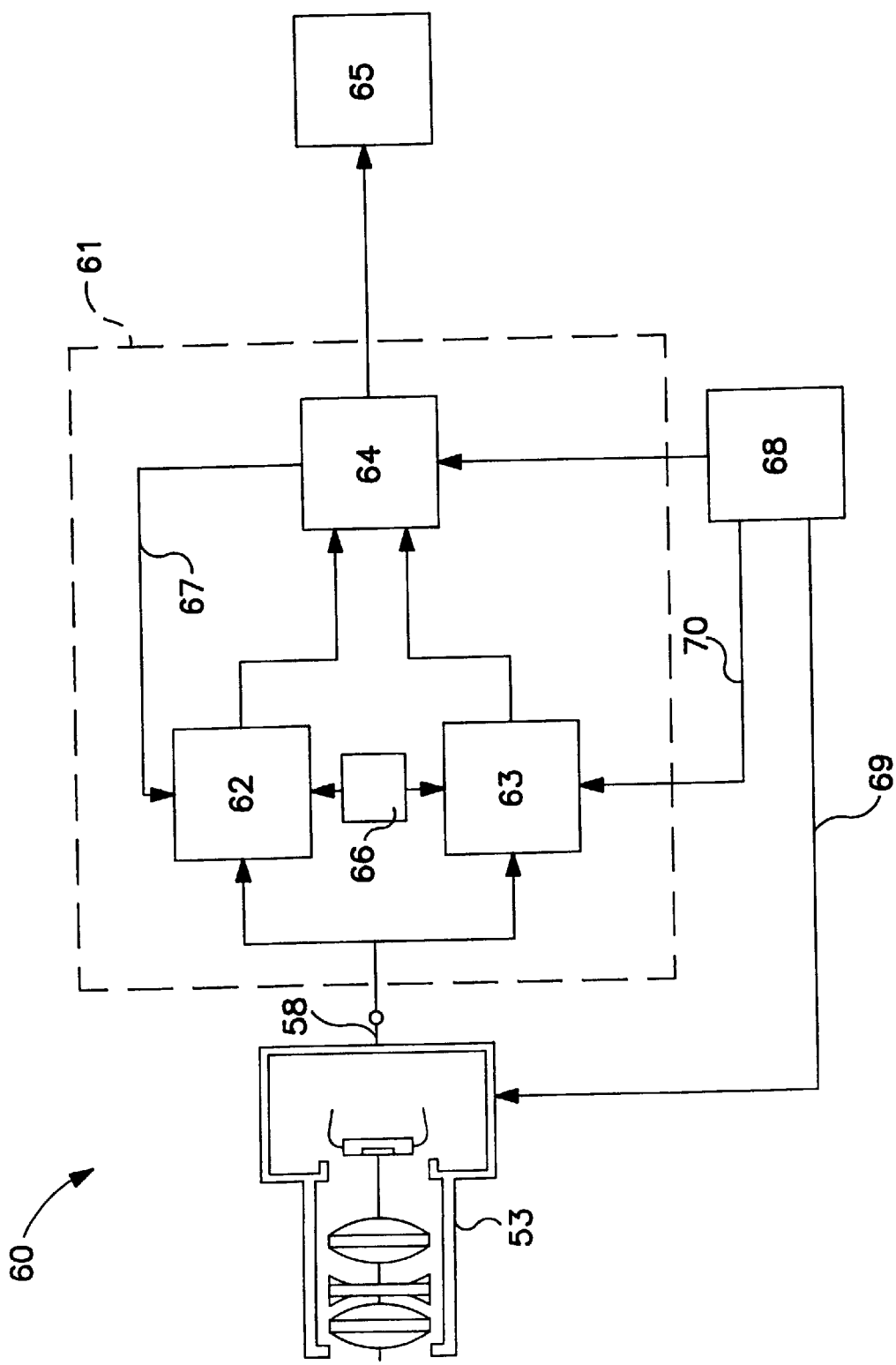
FIG. 6, a schematic block diagram of a device according to the invention.

In the embodiment shown in FIG. 6, the data processing system 61 of the device 60 for carrying out the quality control of an object 10 comprises a storage unit 62, a filter unit 63, an evaluation unit 64 as well as a display element 65, e.g., in the form of a monitor. These components are arranged in such a way that the video output 58 of the line camera 53 is connected with the filter unit 63 as well as the storage unit 62, in which all recorded picture data is stored. The storage unit 62 and the filter unit 63 are connected with the evaluation unit 64, which displays an essentially complete picture of the tested CD on the monitor 65 in accordance with the determined gray scale values of the individual picture points.

The test is carried out in such a way that the CD is completely illuminated during one revolution and all data, i.e., all gray scale values and coordinates of the individual points, are stored in the storage unit 62. The gray scale values of the individual recorded points are either simultaneously or subsequently classified in the filter unit 63, e.g., compared with the gray scale value of the adjacent point, and transmitted to the evaluation unit 64 in case of a predetermined deviation. This procedure is carried out in such a way that the recorded point data is directly classified in the filter unit 63. If a point is classified as being possibly defective, the filter unit 63 transmits the corresponding storage space of this point in the storage unit 62 to the evaluation unit 64. A synchronization device 66 that is connected with the storage unit 62 and the filter unit 63 in order to coordinate the information about the storage space assigned to this point data and transmit said information to the filter unit 63 is provided for this purpose. The evaluation unit 64 subsequently accesses this storage space and possibly the point data of a predetermined region that extends around this marked point in order to evaluate the measured data and classify the possible defect.

In this case, the filter unit 63 consists of a fixed electronic circuit that only carries out simple linkage operations between the gray scale values of a certain low number of points, e.g., between 2 and 10 points. In this context, a fixed circuit represents a circuit that can either not be programmed or only programmed to a limited extent. This is advantageous because the computing speed of nonprogrammable components can be significantly higher than the computing speed of programmable units. Consequently, these functions can also be carried out within a short time by the fixed circuit if large quantities of data are present.

In this case, the evaluation unit 64 can be designed in such a way that it evaluates and examines a larger region originating from a detected point that was classified as being possibly defective so as to detect reliably a possibly existing defect. For this purpose, the evaluation unit is able to retrieve the stored data from the storage unit 62 at any time by means of the signal line 67.

In principle, all recorded data of the tested CD is stored in the storage unit 62 such that said storage unit can be accessed at any time. The individual data is evaluated with different inspection levels. This can be realized in such a way that a lower inspection level is used, e.g., in the lead-out. This means that the measured data is not retrieved by the filter unit 63 or the evaluation unit 64 for each individual point, but rather only for each second or third point. Consequently, it is not required to adjust the camera in accordance with the inspection level. In this case, it is particularly practical if the various coaxial regions 13, 14, 15, 16 of a CD are detected by the evaluation unit 64 based on their different gray scale values such that the inspection level can be automatically adjusted by the evaluation unit 64.

In addition, an input unit 68 that is connected with the evaluation unit 64 and serves for setting certain parameters in order to carry out the measurements is provided. This input unit makes it possible to enter certain predetermined parameters, e.g., the inspection levels within the individual regions. The input unit 68 can, for example, also be connected with the line camera 53 by means of a signal line 69 such that the photosensitive receiver or the optical system can be adapted to different objects that, for example, have a different diameter. In addition, the input unit 68 is also connected with the filter unit 63 by means of a signal line 70 in order to enter the conditions that need to be predetermined for classifying the gray scale values or their linkages.

It is, in principle, possible to link or compare the gray scale values of arbitrary picture points with one another. According to one additional embodiment, it can be practical if the currently scanned picture point is always linked with the precursor of the previous picture point. This measure provides the advantage that even minute variations in the gray scale values by a threshold region can be detected without narrowing the tolerance limits. In addition, it is possible to utilize effectively the currently available video cameras because these cameras have one respective output channel for picture points with an even ordinal number and an output channel for picture points with an odd ordinal number. Consequently, the successive signals of a channel can always be processed in the filter unit because said signals always correspond with the current picture point and the precursor of the previous picture point. Naturally, it is also possible to compare the gray scale value of the current picture point with that of a picture point that was scanned two or more ordinal numbers previously.

In summation, it can be asserted that the filter unit is able to generate a possible defect matrix that serves as the basis for the defect evaluation and makes it possible for the evaluation unit to evaluate exactly and classify the possible defects. The filter unit always processes only a limited number of points such that this preevaluation can be carried out very rapidly, i.e., essentially simultaneously with the scanning process. This means that only a reduced quantity of data needs to be processed, because the complete evaluation only needs to be carried out within the regions that are indicated by the filter unit and possibly limited by the evaluation unit. Consequently, this test method can be carried out within a very short time. This method in particular makes it possible to utilize rapidly operating cameras with a high quantity of picture elements in the receiver because the increased quantity of data so obtained can still be processed within the shortest time.

The device can operate with arbitrary optical scanning devices. It is, in particular, possible that the camera directly record the light beam reflected by the CD without any additional reflection or beam splitting. In addition, it is also possible to use scanning devices in which the incident light beam is projected onto the CD at a right angle.

I claim:

1. Method for carrying out the quality control of an object, in particular a compact disc, in which at least a partial region of the object is scanned by at least one optical scanning system and the gray scale values of the scanned points are recorded, with the gray scale values of at least part of the recorded gray scale values being stored in a storage unit and being evaluated by an evaluation unit, wherein when each of said points is scanned, the scanned point is essentially simultaneously classified as being possibly defective or flawless in a filter unit performing a simple comparison before the evaluation by the evaluation unit in order to determine a possible defective point region of the object, wherein said simple comparison is selected from the group consisting of (a) comparing the gray scale value of the scanned point with the gray scale value of another scanned point, (b) comparing the gray scale value of the scanned point with the gray scale value of an adjacent scanned point, (c) comparing the gray scale value of the scanned point with a predetermined referenced value, (d) comparing the gray scale value of the scanned point with a range of predetermined reference values, (e) linking the gray scale value of the scanned point with at least the gray scale value of another scanned point and comparing the result with a predetermined quantity of reference linkage results, and (f) linking the gray scale value of the scanned point with at least the gray scale value of an adjacent scanned point and comparing the results with a predetermined quantity of reference linkage results; and wherein the point region classified as being possibly defective has a reduced number of points relative to the total number of points scanned and is evaluated by the evaluation unit on the basis of the scanned data of this possibly defective point region stored in the storage unit.

2. Method according to claim 1, wherein the respective gray scale values of the current point and the precursor of the previous point are compared with one another in the filter unit (63).

3. Method according to claim 1, wherein the evaluation is carried out with different inspection levels within the various regions (13, 14, 15, 16) of the object (10).

4. Method according to claim 3, wherein the evaluation unit identifies the various regions (13, 14, 15, 16) of the object (10) based on the different gray scale values of said regions.

5. Method according to claim 1, wherein the optical scanning process is carried out by means of a linear light beam (41), and that the gray scale values are recorded by at least one line camera (53).

6. Method according to claim 5, wherein when testing a rotationally symmetrical object (10), the linear light beam (41) extends radially from the central axis (45), and that the entire surface of the object is scanned with at least 10,000 lines during the course of one revolution.

7. Method according to claim 5, wherein the optical scanning process is carried out within a duration between 0.25 and 2.5 sec during one complete revolution of the object (10).

8. Device for testing an object, in particular a compact disc, comprising at least one scanning element for carrying out an optical scanning process and at least one recording element for recording the gray scale values of the scanned points of at least a partial region of the object, with the recording element being connected with an evaluation unit for the evaluation of the gray scale values of the scanned points and with at least one storage element for storing the measured data of at least part of the scanned points, wherein at least one filter element is provided to essentially simultaneously, as the points are scanned, classify the points as being possibly defective or flawless on the basis of their gray scale values before the evaluation by the evaluation unit, said filter unit being capable of classifying the points by making a simple comparison, said comparison being selected from the group consisting of (a) comparing the gray scale value of the scanned point with the gray scale value of another scanned point, (b) comparing the gray scale value of the scanned point with the gray scale value of an adjacent scanned point, (c) comparing the gray scale value of the scanned point with a predetermined referenced value, (d) comparing the gray scale value of the scanned point with a range of predetermined reference values, (e) linking the gray scale value of the scanned point with at least the gray scale value of another scanned point and comparing the result with a predetermined quantity of reference linkage results, and (f) linking the gray scale value of the scanned point with at least the gray scale value of an adjacent scanned point and comparing the results with a predetermined quantity of reference linkage results.

9. Device according to claim 8, wherein the filter element is selected from the group consisting of a non-programable electronic circuit and an electronic circuit capable of being programmed to only a limited extent.

10. Device according to claim 8, wherein the electronic circuit is switched in such a way that the respective gray scale values of at least two points are linked with one another.

11. Device according to claim 8, wherein the electronic circuit is switched in such a way that the respective gray scale value of at least one point is compared with at least one predetermined reference value and/or range of reference values.

12. Device according to claim 8, wherein the scanning element comprises at least one light source (42) for generating a linear light beam (41).

13. Device according to claim 8 wherein the recording element (53) comprises a linear photosensitive receiver (54).

14. Method according to claim 6, wherein the optical scanning process is carried out within a duration between 0.25 and 2.5 sec during one complete revolution of the object (10).

15. Device according to claim 9, wherein the electronic circuit is switched in such a way that the respective gray scale values of at least two points are linked with one another.

16. Device according to claim 9, wherein the electronic circuit is switched in such a way that the respective gray scale value of at least one point is compared with at least one predetermined reference value and/or range of reference values.

17. Method for carrying out a high-speed inspection of an optical disc, consisting essentially of the steps of:

scanning at least a portion of the optical disc with an optical scanning system to record only a single gray scale value for each scanned point in said portion;

storing only said recorded single gray scale value for each scanned point in a storage unit;

classifying with a high-speed filter unit each of said recorded gray scale values as being either possibly defective or flawless in order to identify a possibly defective point region of said portion of the optical disc; and evaluating with an evaluation unit said recorded gray scale values stored in said storage unit of only said possibly defective point regions identified in said classifying step;

wherein said filter unit performs only simple comparisons between gray scale values to identify a predetermined deviation, said simple comparisons being selected from the group consisting of (a) comparing the gray scale value of the scanned point with the gray scale value of another scanned point, (b) comparing the gray scale value of the scanned point with the gray scale value of an adjacent scanned point, (c) comparing the gray scale value of the scanned point with a predetermined referenced value, (d) comparing the gray scale value of the scanned point with a range of predetermined reference values, (e) linking the gray scale value of the scanned point with at least the gray scale value of another scanned point and comparing the result with a predetermined quantity of reference linkage results, and (f) linking the gray scale value of the scanned point with at least the gray scale value of an adjacent scanned point and comparing the results with a predetermined quantity of reference linkage results;

whereby said filter unit limits the amount of data required to be processed by said evaluation unit to enable high-speed inspection.

* * * * *